(12) United States Patent
Ponzi (10) Patent No.: US 7,806,872 B2
(45) Date of Patent: *Oct. 5, 2010

(54) INJECTION CATHETER WITH NEEDLE STOP (75) Inventor: Dean M. Ponzi, Glendora, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/428,647

(22) Filed: May 2, 2003

(65) Prior Publication Data

US 2003/0195470 A1  Oct. 16, 2003

Related U.S. Application Data (63) Continuation of application No. 09/563,769, filed on May 1, 2000, now Pat. No. 6,623,474, and a continuation-in-part of application No. 09/280,202, filed on Mar. 29, 1999, now Pat. No. 6,165,164.

(60) Provisional application No. 60/165,354, filed on Nov. 12, 1999, provisional application No. 60/088,019, filed on Jun. 4, 1998, provisional application No. 60/088,984, filed on Jun. 11, 1998.

(51) Int. Cl.
*A61M 5/178* (2006.01)
(52) U.S. Cl. .............................. 604/164.07; 604/95.03; 604/95.04; 604/173
(58) Field of Classification Search ................. 604/528, 604/523, 525, 264, 167.07, 117, 272, 164–174, 604/192–98, 256, 95–96, 102–115; 606/41–52
See application file for complete search history.

(56) References Cited

U.S. PATENT DOCUMENTS 3,598,119 A   8/1971   White (Continued)

FOREIGN PATENT DOCUMENTS

EP   0826387 A2   3/1998

(Continued)

OTHER PUBLICATIONS

European Search Report dated May 7, 2004 for European Application No. 03258245.4-1526, 5 pgs.

(Continued)

*Primary Examiner*—Kevin C Sirmons
*Assistant Examiner*—Phillip Gray
(74) *Attorney, Agent, or Firm*—Christie, Parker & Hale, LLP (57) ABSTRACT An injection catheter is provided. The catheter comprises a catheter body comprising a flexible tubing having proximal and distal ends and at least one needle passage extending therethrough. The needle passage has a proximal region having a proximal diameter and a distal region having a distal diameter less than the proximal diameter. A needle control handle is provided at the proximal end of the catheter body. An injection needle extends through the catheter body and needle control handle and has a proximal end within the needle control handle and a distal end within the needle passage. The injection needle is longitudinally slidable within the catheter body so that its distal end can extend beyond the distal end of the catheter body. A needle stop is mounted on a portion of the injection needle that is positioned within the proximal region of the needle passage. The needle stop has a distal end that is sized to prevent passage of the portion of the injection needle on which the needle stop is mounted from passing into the distal region of the needle passage. The needle stop limits the distance that the injection needle can be extended beyond the distal end of the catheter body.

16 Claims, 9 Drawing Sheets

U.S. PATENT DOCUMENTS

| | | | |
|---|---|---|---|
| 4,006,744 A * | 2/1977 | Steer .................... 604/533 |
| 4,270,535 A | 6/1981 | Bogue et al. |
| 4,578,061 A | 3/1986 | Lemelson |
| 5,244,460 A | 9/1993 | Unger et al. |
| 5,336,222 A | 8/1994 | Durgin, Jr. et al. |
| 5,354,279 A | 10/1994 | Hofling |
| 5,385,148 A | 1/1995 | Lesh et al. |
| 5,403,311 A | 4/1995 | Abele et al. |
| 5,419,777 A | 5/1995 | Hofling |
| 5,431,168 A | 7/1995 | Webster, Jr. |
| 5,431,649 A | 7/1995 | Mulier et al. |
| 5,464,395 A | 11/1995 | Faxon et al. |
| 5,522,815 A | 6/1996 | Durgin, Jr. et al. |
| 5,531,780 A * | 7/1996 | Vachon .................... 607/120 |
| 5,588,432 A | 12/1996 | Crowley |
| 5,661,133 A | 8/1997 | Leiden et al. |
| 5,725,524 A | 3/1998 | Mulier et al. |
| 5,741,320 A | 4/1998 | Thornton et al. |
| 5,797,870 A | 8/1998 | March et al. |
| 5,810,804 A | 9/1998 | Gough et al. |
| 5,833,715 A | 11/1998 | Vachon et al. |
| 5,857,997 A | 1/1999 | Cimino et al. |
| 5,876,340 A | 3/1999 | Tu et al. |
| 5,891,138 A | 4/1999 | Tu et al. |
| 5,906,594 A * | 5/1999 | Scarfone et al. ........ 604/165.01 |
| 5,906,613 A | 5/1999 | Mulier et al. |
| 5,921,982 A | 7/1999 | Lesh et al. |
| 6,126,633 A | 10/2000 | Kaji et al. |
| 6,165,164 A * | 12/2000 | Hill et al. .................... 604/523 |
| 6,179,809 B1 * | 1/2001 | Khairkhahan et al. .... 604/95.04 |
| 6,241,710 B1 | 6/2001 | VanTassel et al. |
| 6,575,931 B1 * | 6/2003 | Ponzi ...................... 604/95.01 |
| 6,623,473 B1 * | 9/2003 | Ponzi ........................ 604/528 |
| 6,623,474 B1 * | 9/2003 | Ponzi ........................ 604/528 |
| 2002/0183720 A1 | 12/2002 | Hill et al. |
| 2002/0183738 A1 | 12/2002 | Chee et al. |

FOREIGN PATENT DOCUMENTS

| | | |
|---|---|---|
| EP | 1099453 A2 | 5/2001 |
| JP | 2-139649 | 11/1990 |
| JP | 8504613 T | 5/1996 |
| JP | 11239619 A | 9/1999 |

OTHER PUBLICATIONS

Marhsall, D.J. et al., "Biocompatibility of Cardiovascular Gene Delivery Catheters with Adenovirus Vectors: An Important Determinant of the Efficiency of Cardiovascular Gene Transfer", Molecular Therapy, vol. 1, No. 5, May 2000, Part 1 of 2 Parts, pp. 423-429.

* cited by examiner

INJECTION CATHETER WITH NEEDLE STOP

CROSS-REFERENCE TO RELATED APPLICATIONS

This application is a continuation of U.S. patent application Ser. No. 09/563,769, filed May 1, 2000 now U.S. Pat. No. 6,623,474, which claims the benefit of U.S. Provisional Patent Application No. 60/165,354, filed Nov. 12, 1999; U.S. patent application Ser. No. 09/563,769 is also a continuation-in-part of U.S. patent application Ser. No. 09/280,202, filed Mar. 29, 1999, now U.S. Pat. No. 6,165,164, which claims the benefit of U.S. Provisional Patent Application Nos. 60/088,019, filed Jun. 4, 1998 and 60/088,984, filed on Jun. 11, 1998, the entire disclosures of which are incorporated herein by reference.

FIELD OF THE INVENTION

This invention relates to a catheter for infusing therapeutic or diagnostic agents into the tissue of organs, and more particularly to a catheter having a mechanism for controlled extension of an injection needle.

BACKGROUND OF THE INVENTION

Targeted delivery of therapeutic or diagnostic agents, such as occurs in gene therapy, is very desirable but often presents a difficult challenge. A potential benefit of targeted delivery is that there is an increased efficiency obtained by the precise placement of the therapeutic agent. There are several problems to his procedure which must be overcome in order to obtain satisfactory results from such therapy, such as the problems of obtaining access to the delivery site, transporting the therapeutic agent to the desired site, injecting the therapeutic agent at the proper depth within the organ tissue, steering the distal end of the catheter to a desired location within the organ prior to infusing the agent, and positioning the distal tip of the catheter at precisely the same location where prior measurements have indicated that the drug should be infused. It is also important to for a physician to be able to monitor the position of the infusion needle with respect to the wall of the organ. In the case of an organ, such as the heart, in which the walls are in constant motion, the activity of positioning and monitoring the position of the distal tip of the catheter, or infusion needle, becomes especially difficult.

U.S. Pat. No. 3,598,119 discloses a medical device for injecting drugs in which the injection needle is guided through an inner lumen of a catheter for insertion of the needle under skin tissue. A bladder at the distal end of the catheter may be inflated through another lumen for holding the point of the needle point in a fixed position beneath the skin.

U.S. Pat. No. 4,578,061 discloses a catheter for injecting a liquid into a vein, or artery, through an injection needle which is longitudinally movable beyond the distal end of the catheter. A dual chamber system is utilized within the catheter tip to provide for movement of a plunger to extend the injection needle and also to allow for a plunger to be used to apply a predetermined dose of medication through the injection needle.

U.S. Pat. No. 4,578,061 discloses an injection catheter having a longitudinal movable needle which may be moved through a lumen in order to extend out of the side wall of the catheter for injecting a liquid into a blood vessel. The needle is normally retracted into the device so that the needle will not penetrate tissue as the device is moved through a body duct. Thereafter, the needle is moved out of the side of the catheter into a vessel wall in order to infuse a liquid into the wall of a vessel.

U.S. Pat. No. 5,244,460 is directed toward a method for improving blood flow to the heart. More particularly this patent is directed toward a medical procedure for improving the growth of cardiac blood vessels by inserting a catheter into a coronary artery and injecting into the heart a blood vessel growth promoting peptide through an injection port of the catheter.

U.S. Pat. No. 5,419,777 is directed toward a catheter for injection of a fluid into body cavities such as coronary vessels and arteries. This patent, as is the case with the '061 patent, illustrates the use of an injection needle which protrudes laterally through the side walls of the distal tip of the catheter. In the case of drug injections to be made into coronary vessels and arteries, it is very desirable to have the needles extend out of the side walls of the catheter and at an acute angle to the walls of the vessel in order to penetrate the walls of the vessel for injection of the agent.

U.S. Pat. No. 5,431,168, assigned to the same assignee as the present patent application, is directed toward a steerable catheter which includes a puller wire for controlling the distal end of the catheter from a control handle which is mounted on the proximal end of the catheter.

Copending U.S. patent application Ser. No. 09/019,453, entitled "Intracardiac Drug Delivery," assigned to an affiliated company of the assignee of this application, discloses an injection catheter system for infusing a diagnostic or therapeutic agent into the wall of an organ which includes an electromagnetic sensor disposed within the distal tip of the catheter for providing very precise location information for the distal tip of the catheter. The subject matter of this copending patent application is incorporated by reference into the subject patent application.

Copending U.S. patent application Ser. No. 09/280,202 discloses an injection catheter where extension of the injection needle is determined by the amount of movement that is allowed in the injection handle. The injection handle is adjustable, permitting the physician to adjust the needle extension to the desired length. Although this design has several advantages, it can cause the needle to buckle inside the catheter due to frictional force between the needle and the housing in which the needle is mounted, which can result in unpredictable needle extension.

SUMMARY OF THE INVENTION

The present invention is directed to a catheter for infusing therapeutic or diagnostic agents into the tissue of organs having a system for predicable extension of the infusion needle, thereby reducing the variability that can occur when the extent of the needle extension is controlled by the needle control handle.

In one embodiment, the invention is directed to a catheter comprising a catheter body comprising a flexible tubing having proximal and distal ends and at least one needle passage extending therethrough. The needle passage has a proximal region having a proximal diameter and a distal region having a distal diameter less than the proximal diameter. A needle control handle is provided at the proximal end of the catheter body. An injection needle extends through the catheter body and needle control handle and has a proximal end within the needle control handle and a distal end within the needle passage. The injection needle is longitudinally slidable within the catheter body so that its distal end can extend beyond the distal end of the catheter body. A needle stop is mounted on a portion of the injection needle that is positioned within the proximal region of the needle passage. The needle stop has a distal end that is sized to prevent passage of the portion of the injection needle on which the needle stop is mounted from passing into the distal region of the needle passage. The needle stop limits the distance that the injection needle can be extended beyond the distal end of the catheter body.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
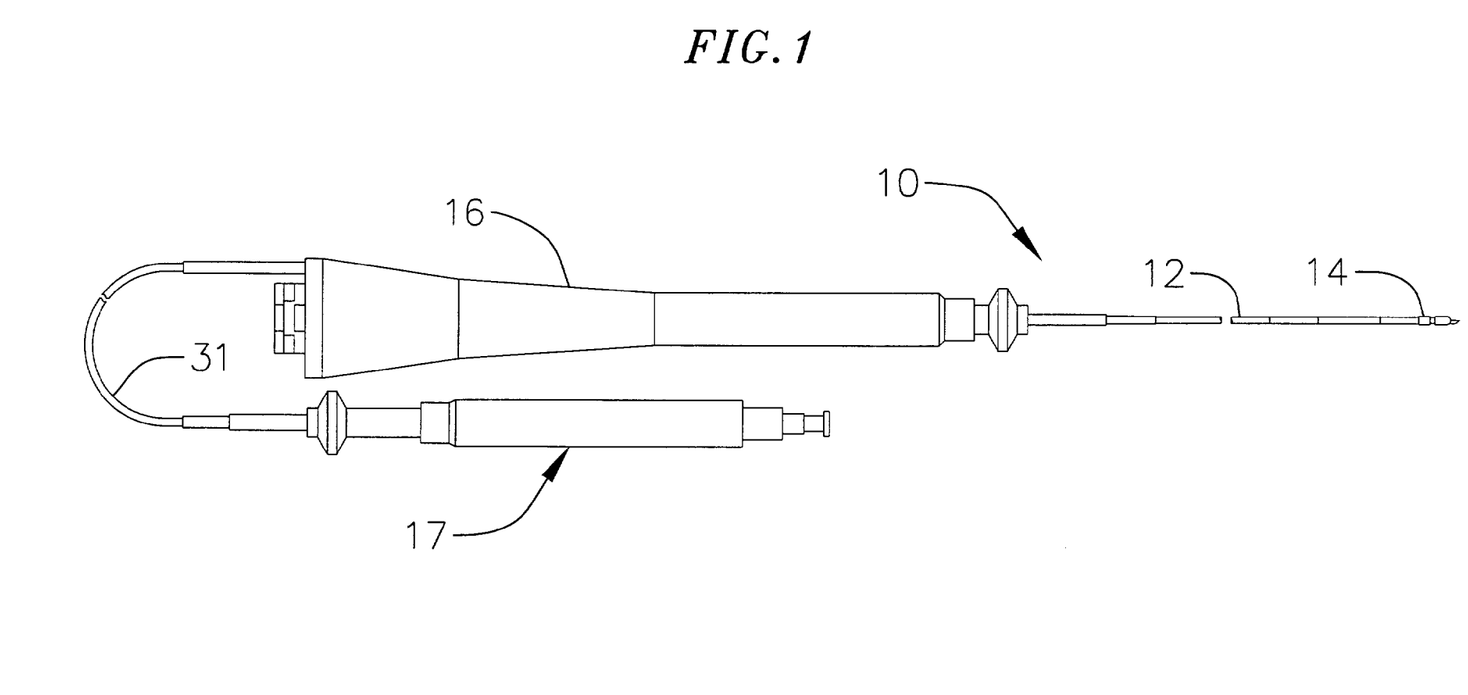
FIG. 1 is a side plan view of one embodiment of the catheter of the present invention.

In a preferred embodiment of the invention, there is provided a catheter for use for injection of a therapeutic or diagnostic agent into the heart. As shown in FIG. 1, catheter 10 comprises an elongated catheter body 12 having proximal and distal ends, a tip section 14 at the distal end of the catheter body 12, a deflection control handle 16 at the proximal end of the catheter body 12, and a needle control handle 17 proximal the catheter body.

Figure 5:
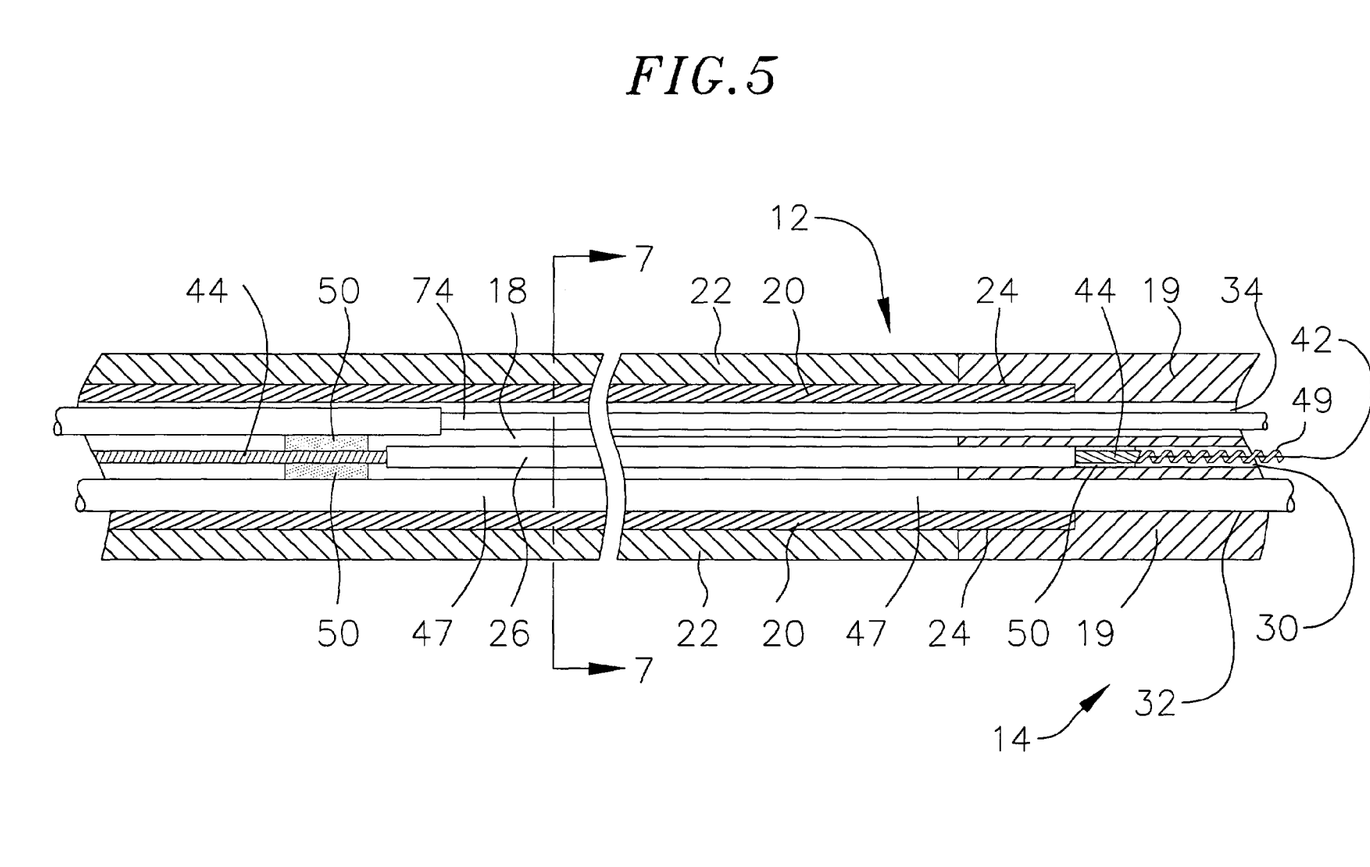
FIG. 5 is a side cross-sectional view of the catheter body, including the junction between the catheter body and the section.
Figure 7:
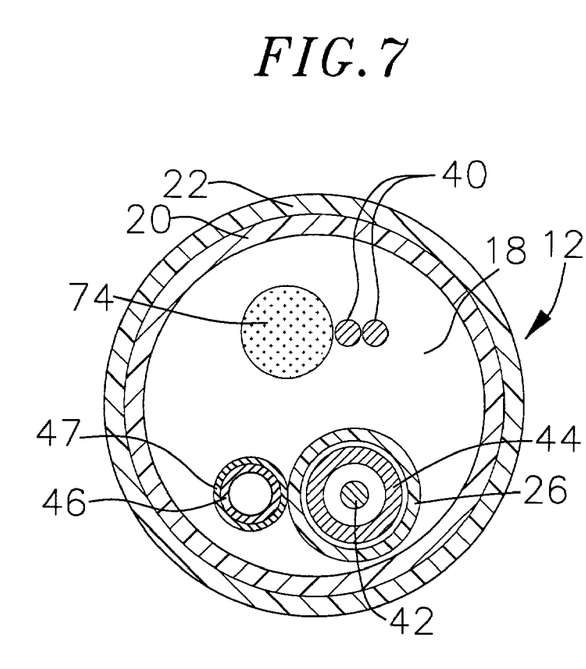
FIG. 7 is a transverse cross-sectional view of the catheter body along line 7-7.

With reference to FIGS. 5 and 7, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used. If desired, the stiffening tube 20 can be eliminated.

Figure 3:
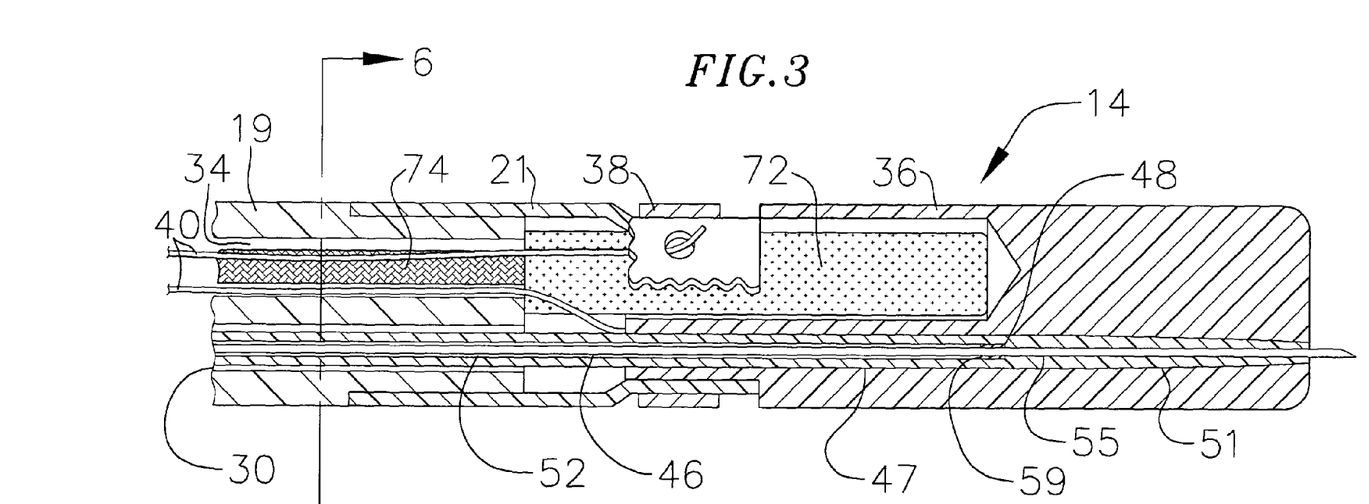
FIG. 3 is a side cross-sectional view of a tip section according to the invention having three lumens, showing the injection needle and a needle stop.
Figure 3A:
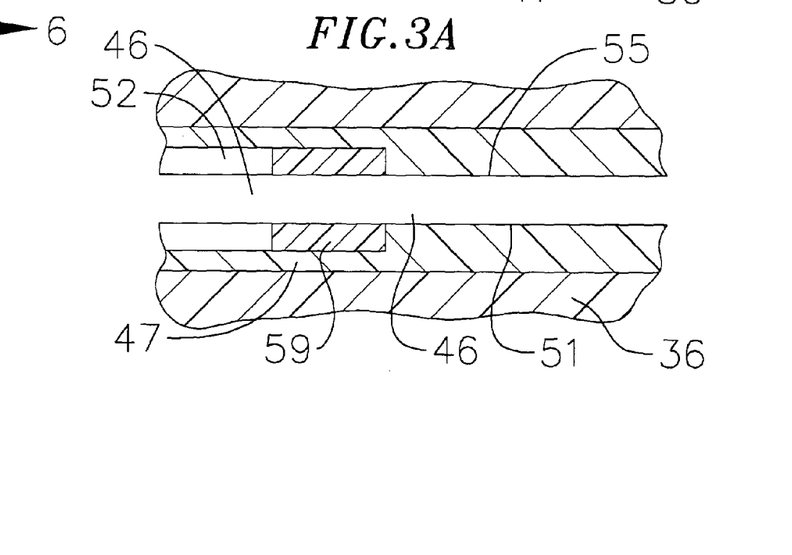
FIG. 3A is an enlarged view of the needle stop of FIG. 3.
Figure 4:
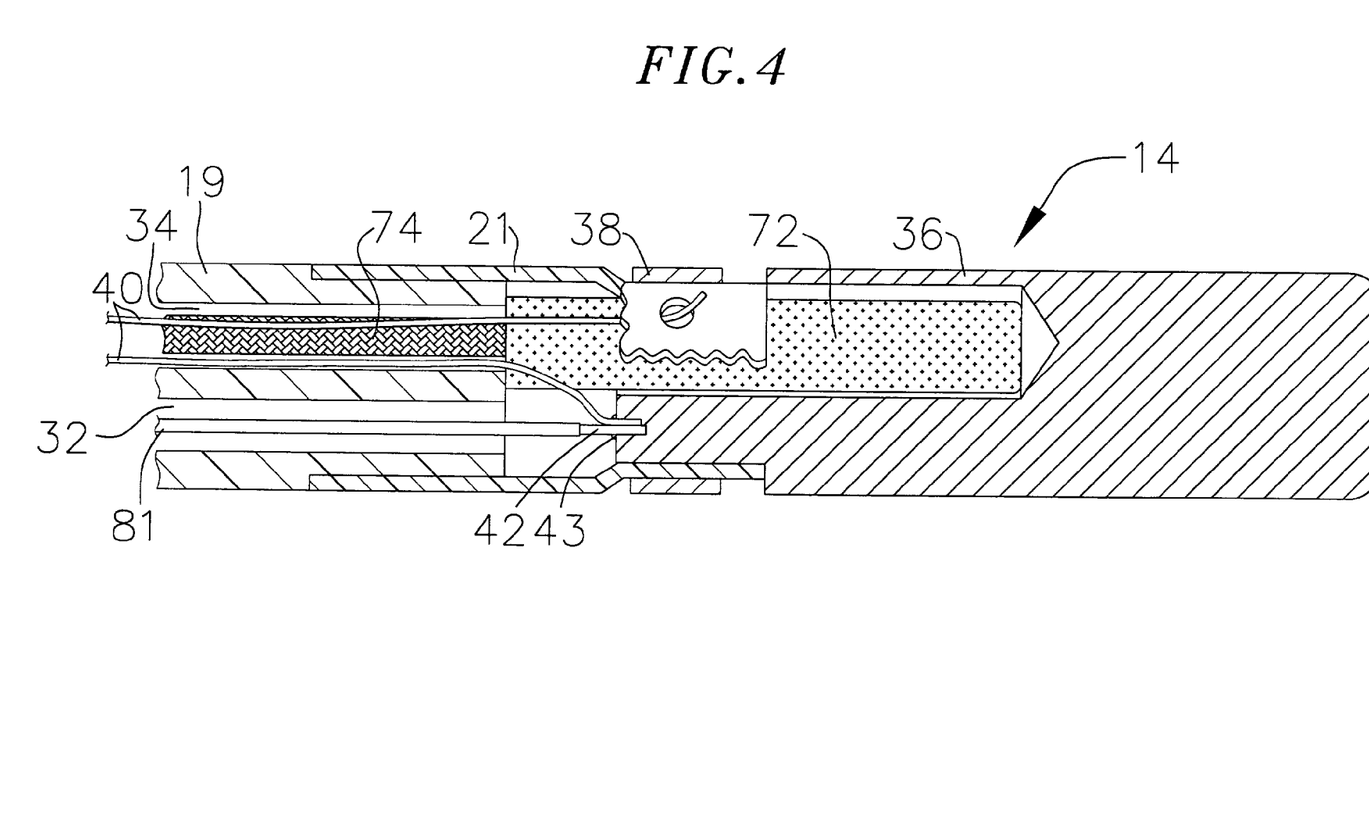
FIG. 4 is a side cross-sectional view of the tip section of FIG. 3 showing the position of the electromagnetic mapping sensor and the puller wire.
Figure 6:
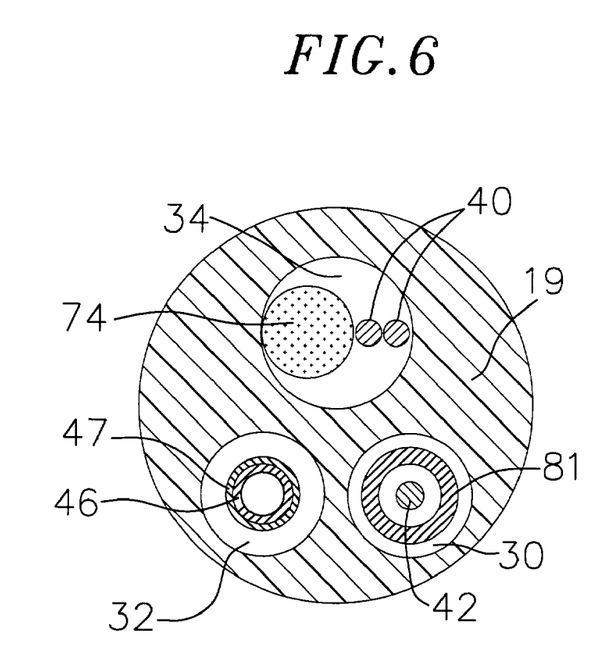
FIG. 6 is a transverse cross-sectional view of the tip section of FIG. 3 along line 6-6 showing an embodiment having three lumens.

As shown in FIGS. 3, 4 and 6, the tip section 14 comprises a short section of tubing 19 having three lumens 30, 32 and 34. The tubing 19 is made of a suitable non-toxic material which is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 French. The size of the lumens is not critical. In a particularly preferred embodiment, the tip section has an outer diameter of about 7 French (0.092 inch) and the first lumen 30 and second lumen 32 are generally about the same size, having a diameter of about 0.022 inch, with the third lumen 34 having a slightly larger diameter of about 0.036 inch.

If desired, the flexible tubing 19 of the tip section 14 can be eliminated, and the catheter body 12 can be provided with a single lumen, as described, or multiple lumens, as desired.

A preferred means for attaching the catheter body 12 to the tip section 14 is illustrated in FIG. 5. The proximal end of the tip section 14 comprises an inner counter bore 24 that receives the outer surface of the polyimide stiffener 20. The tip section 14 and catheter body 12 are attached by glue or the like.

The stiffening tube 20 is held in place relative to the outer wall 22 at the proximal end of the catheter body 12. In preferred construction of the catheter body 12, a force is applied to the proximal end of the stiffening tube 20 which causes the distal end of the stiffening tube 20 to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane. Any other suitable method of attaching the catheter body 12 to the tip section 14 can be used.

Extending through the single lumen 18 of the catheter body 12 are lead wires 40, an injection needle 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the injection needle 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either for which are undesirable performance characteristics.

With reference to FIGS. 3 and 4, mounted at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. Alternatively, the tip electrode 36 can be mounted directly to the distal end of the flexible tubing 19 of the tip section 14.

Mounted on the distal end of the plastic housing 21 is a ring electrode 38. The ring electrode 38 is slid over the plastic housing 21 and fixed in place by glue or the like. If desired, additional ring electrodes may be used and can be positioned over the plastic housing 21 or over the flexible tubing 19 of the tip section 14.

The tip electrode 36 and ring electrode 38 are each connected to a separate lead wire 40. The lead wires 40 extend through the third lumen 34 of tip section 14, the catheter body 12, and the control handle 16, and terminate at their proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

The lead wires 40 are attached to the tip electrode 36 and ring electrode 38 by any conventional technique. Connection of lead wire 40 to the tip electrode 36 is preferably accomplished by weld 43, as shown in FIG. 4.

A puller wire 42 is provided for deflection of the tip section 14. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

As discussed above, a compression coil 44 is provided in surrounding relation to a portion of the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and any of the lead wires 40, injection needle 46 or sensor cable 74. A non-conductive sheath 26 made of polyimide tubing is presently preferred.

The compression coil 44 is anchored at its proximal end to the proximal end of the stiffening tube 20 in the catheter body 12 by glue to form a glue joint 50 and at its distal end to the tip section 14 in the second lumen 32, also forming a glue joint 50. The glue may be applied by means of a syringe or the like through a hole made between the outer surface of the catheter body 12 and the single lumen.

The puller wire 42 extends into the second lumen 32 of the tip section 14. The distal end of the puller wire 42 is anchored to the tip electrode 36 or to the side of the catheter tip section 14. With reference to FIGS. 4 and 5, within the tip section 14, and distal to the glue joint 50, the turns of the compression coil are expanded longitudinally. Such expanded turns 49 are both bendable and compressible and preferably extend for a length of about 0.5 inch. The puller wire 42 extends through the expanded turns 49 then into a plastic, preferably Teflon®, sheath 81, which prevents the puller 42 from cutting into the wall of the tip section 14 when the section 14 is deflected.

An injection needle 46 is provided, which extends from the needle control handle through the catheter body 12, through the first lumen 30 of the tip section 14 and through a passage 51 in the tip electrode 36. As illustrated in FIG. 3, the injection needle 46 is preferably formed with a beveled edge at the distal tip of the needle.

In one embodiment, the injection needle 46 is formed of Nitinol. Alternatively, the injection needle 46 is formed of plastic, or a portion of the needle is formed of plastic and another portion of the needle is formed of metal, such as Nitinol, as described in more detail in copending U.S. patent application entitled "Catheter with Injection Needle," to Dean Ponzi, filed on even date herewith, the entire disclosure of which is incorporated herein by reference. If desired, the injection needle 46 can be provided with one or more fluid openings along its length to permit fluid flow out the side of the needle as well as out the distal end, as also described in copending U.S. patent application entitled "Catheter with Injection Needle."

The needle 46 is coaxially mounted within a protective tube 47, preferably made of polyimide, which serves to prevent the needle from buckling and also serves to electrically insulate the needle from the distal electrode 36. The protective tube 47 additionally serves to provide a fluid-tight seal surrounding the distal end of the injection needle 46. FIG. 3 depicts the injection needle 46 extending beyond the distal end of the tip electrode 36, as it would be positioned in order to infuse diagnostic or therapeutic fluid into the human heart. The distal end of the injection needle 46 is withdrawn into the tip electrode 36 during the period of time that the catheter is inserted through the vasculature of the body and also during the period of time in which the catheter is removed from the body to avoid injury. Alternatively, the tip section 14 can be provided without a tip electrode 36, in which case the distal end of the injection needle 46 could be retracted into the first lumen 30 of the tip section 14. In either embodiment, the injection needle 46 is extendable and retractable beyond the distal end of the catheter.

In the depicted embodiment, the inner region of the protective tube 47 serves as a needle passage. The needle passage has a proximal region 52 with a proximal diameter and a distal region 55 with a distal diameter that is less than the proximal diameter. The distal diameter is approximately equal to the outer diameter of the injection needle 46 to provide a fluid-tight seal, as described above. This design creates a step 48 at the distal end of the proximal region 52. A needle stop 59 is mounted on a portion of the injection needle 46 that is positioned within the proximal region 52 of the needle passage. The needle stop 59 is sized to prevent passage of the portion of the injection needle on which the needle stop is mounted from passing into the distal region 55 of the needle passage. In the embodiment depicted in FIG. 3, the needle stop 59 is in the form of a collar that is mounted in surrounding relation to the injection needle 46. The collar extends only a short length along the needle, e.g., a distance ranging from about 0.01 inch to about 0.75 inch.

This design limits the distance that the injection needle 46 can extend beyond the distal end of the tip section 14. As described in more detail below, needle extension and retraction is accomplished with the needle control handle. When the injection needle 46 is moved distally using the needle control handle, it pushes the needle stop 59 distally into the step 48 at the distal end of the proximal region 52. The interaction between the needle stop 59 and the step 48 prevents further distal movement of the injection needle 46, thereby limiting the extent to which the needle can extend beyond the distal end of the tip section 14. This design ensures that the needle always extends out of the tip section 14 the same distance, regardless of whether the tip section is straight or deflected.

Figure 9:
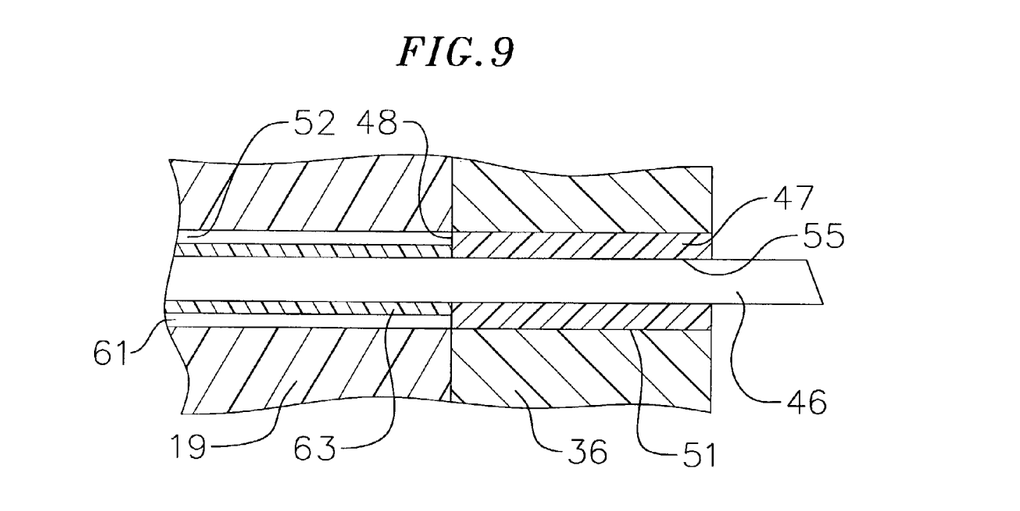
FIG. 9 is a schematic partial side cross-sectional view of a tip section showing an alternative needle stop design in accordance with the invention.

FIG. 9 depicts an alternative design for the needle passage and needle stop. In this embodiment, a lumen 61 in the tubing 19 of the tip section 14 serves as the proximal region 52 of the needle passage. As in the embodiment of FIG. 3, a passage 51 is provided in the tip electrode 36. Within the tip electrode 36, the needle 46 is coaxially mounted within a protective tube 47, although the protective tube does not extend into the lumen 61. The inner region of the protective tube 47 serves as the distal region 55 of the needle passage. The inner diameter of the lumen 61 is thus larger than the inner diameter of the protective 47, thus creating a step 48 at the distal end of the lumen. An elongated tube 63, preferably having a length of at least about 2 inches, is coaxially mounted around a portion of the injection needle 46 that is in the proximal region 52. The elongated tube 63 can be made of any suitable material, such as plastic or Nitinol. The elongated tube 63 has an diameter greater than the inner diameter of the protective tube 47, and thus serves as a needle stop in a manner similar to the collar described above.

The needle stop 59 need not be coaxially mounted on the injection needle 46. For example, the needle stop could be in the form of a rectangular tab that is mounted on only a portion of the circumference of the injection needle 46. Any other suitable design can be provided for the needle stop 59, so long as the needle stop is of a size and shape so that it cannot pass into the distal region 55 of the needle passage.

Figure 10:
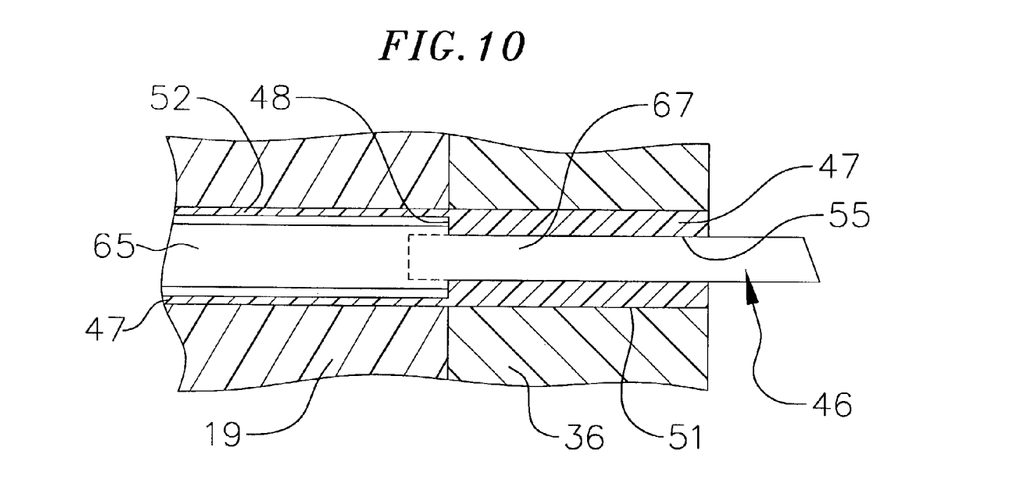
FIG. 10 is a schematic partial side cross-sectional view of a tip section showing another alternative needle stop design in accordance with the invention.

In another alternative design, as shown in FIG. 10, the needle stop 59 is integral with the injection needle 46. In this embodiment, the injection needle 46 is formed of two pieces of tubing, a proximal tubing 65 and a distal tubing 67, each of which can be made of any suitable material as described above, such as metal or plastic. The proximal end of the distal tubing 67 is bonded or otherwise attached to the distal end of the proximal tubing 65. Preferably the proximal end of the distal tubing 67 is inserted into the distal end of the proximal tubing 65 and attached by polyurethane glue or the like. The proximal tubing 65 has an outer diameter greater than the outer diameter of the distal tubing 67 and greater than the inner diameter of the distal region 55 of the needle passage. The proximal tubing thus acts as the needle stop 59.

The needle passage can be formed by any suitable combination of elements in the tip section so long as it has a proximal region 52 with a proximal diameter and a distal region 55 with a distal diameter that is less than the proximal diameter. Thus, the needle passage can be formed from a tubing that is separate from the tip section 14, as shown, for example, in FIGS. 3 and 10, discussed above. Alternatively, the needle passage can be formed directly in the tip section 14 and tip electrode 36, or directly in the tip section only if no tip electrode is provided. In another alternative, a combination of these approaches can be provided, for example, as shown in FIG. 9 discussed above.

Additionally, an electromagnetic sensor 72 is contained within the distal end of the tip section 14. The electromagnetic sensor 72 is connected to an electromagnetic sensor cable 74, which extends through the third lumen 34 of the tip section 14 through the catheter body 12 into the control handle 16. The electromagnetic sensor cable 74 comprises multiple wires encased within a plastic sheath. In the control handle 16, the wires of the sensor-cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. Suitable electromagnetic sensors for use in connection with the present invention are described, for example, in U.S. Pat. No. 5,391,199 and U.S. patent application Ser. No. 09/160,063, entitled "Miniaturized Position Sensor," the disclosures of which are incorporated herein by reference. A preferred electromagnetic mapping sensor 72 is manufactured by Biosense Webster, Inc. and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the injection catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or more preferably in combination with the tip electrode 36 and ring electrode 38. By combining the electromagnetic sensor 72 and electrodes 36 and 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and the extent of catheter displacement. The tip electrode 36 and ring electrode 38 are used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement. Hence, the combination of the electromagnetic mapping sensor 72 and tip and ring electrodes 36 and 38 is used as a diagnostic catheter to determine whether and where to infuse a drug into the wall of the heart. Once the presence and location of ischemic tissue has been identified, the tip section 14 of the catheter can be deflected so that the injection needle 46 is generally normal, i.e., at a right angle, to the ischemic tissue, and the injection needle may then be extended out of the distal end of the tip electrode 36 and into the wall of the heart.

It is understood that, while it is preferred to include both electrophysiology electrodes and an electromagnetic sensor in the catheter tip, it is not necessary to include both. For example, an injection catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

The electrode lead wires 40 and electromagnetic sensor cable 74 must be allowed some longitudinal movement within the catheter body so that they do not break when the tip section 14 is deflected. To provide for such lengthwise movement, there is provided a tunnel through the glue joint 50, which fixes the proximal end of the compression coil 44 inside the catheter body 12. The tunnel is formed by a transfer tube 27, preferably made of a short segment of polyimide tubing. Preferably the transfer tube is approximately 60 mm long and has an outer diameter of about 0.021 inch and an inner diameter of about 0.019 inch.

Figure 8:
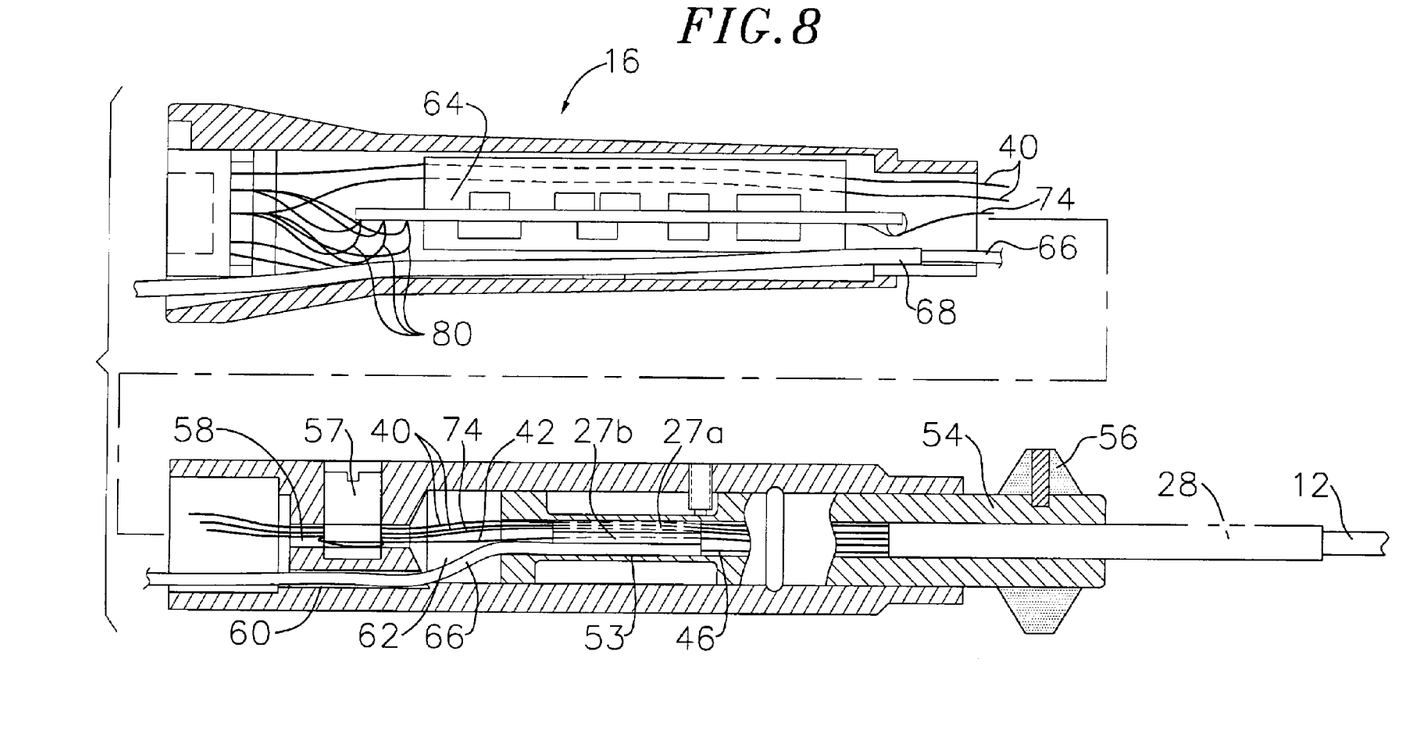
FIG. 8 is a side cross-sectional view of the catheter handle.

Longitudinal movement of the puller wire 42 relative to the catheter body 12, which results in deflection of the tip section 12, is accomplished by suitable manipulation of the control handle 16. As shown in FIG. 8, the distal end of the control handle 16 comprises a piston 54 with a thumb control 56 for manipulating the puller wire 42. The proximal end of the catheter body 12 is connected to the piston 54 by means of a shrink sleeve 28.

The injection needle 46 within the protective tube 47, the puller wire 42, the lead wires 40 and the electromagnetic sensor cable 74 extend through the piston 54. The puller wire 42 is anchored to an anchor pin 57 located proximal to the piston 54. The lead wires 40 and electromagnetic sensor cable 74 extend through a first tunnel 58, located near the side of the control handle 16. The electromagnetic sensor cable 74 connects to the circuit board 64 in the proximal end of the control handle. Wires 73 connect the circuit board 64 to a computer and imaging monitor (not shown).

The injection needle 46 and protective tube 47 extend through a guide tube 66, preferably made of polyurethane, and are afforded longitudinal movement therein. The guide tube 66 is anchored to the piston 54, preferably by glue at glue joint 53. This design allows the needle 46 and protective tube 47 longitudinal movement within the control handle 16 so that the needle 46 does not break when the piston 54 is adjusted to manipulate the puller wire 42. Within the piston 54, the electromagnetic sensor cable 74 and lead wires 40 are situated within a transfer tube 27a, and the puller wire 42 is situated within another transfer tube 27b to allow longitudinal movement of the wires and cable near the glue joint 53.

The injection needle 46, protective tube 47 and guide tube 66 extend through a second tunnel 60 situated near the side of the control handle 16 opposite the anchor pin 36. To avoid undesirable bending of the injection needle 46, a space 62 is provided between the proximal end of the piston 54 and the distal end of the second tunnel 60. Preferably the space 62 has a length of at least 0.50 inch and more preferably about from about 0.60 inch to about 0.90 inch.

In the proximal end of the control handle 16, the injection needle 46, protective tube 47 and polyurethane guide tube 66 extend through a second larger plastic guide tube 68, preferably made of Teflon®, which affords the guide tube 66, injection needle 46, and protective tube 47 longitudinal slidable movement. The second guide tube 68 is anchored to the inside of the control handle 16 by glue or the like and extends proximally beyond the control handle 16. The second guide tube 68 protects the injection needle 46 both from contact with the circuit board 64 and from any sharp bends as the guide tube 66, needle 46, and protective tube 47 emerge from the control handle 16.

Figure 2A:
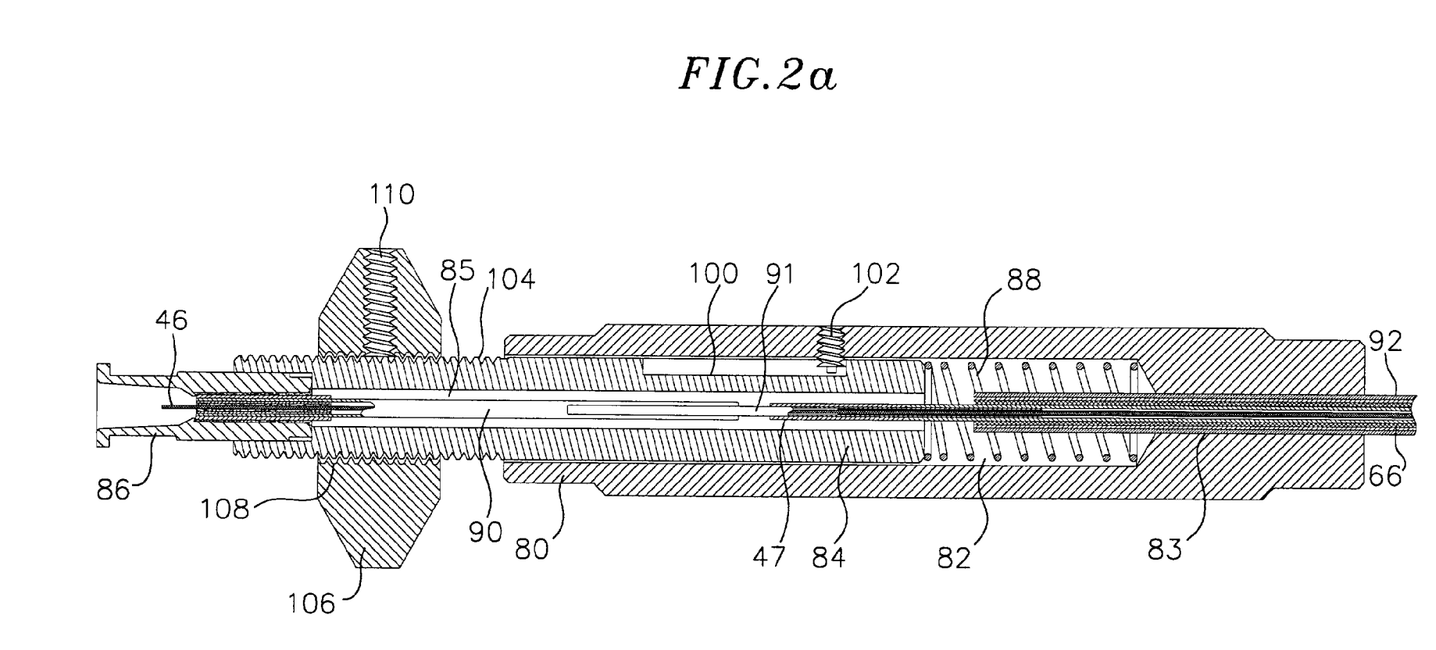
FIG. 2a is a side cross-sectional view of the needle control handle where the needle is in a retracted position.
Figure 2B:
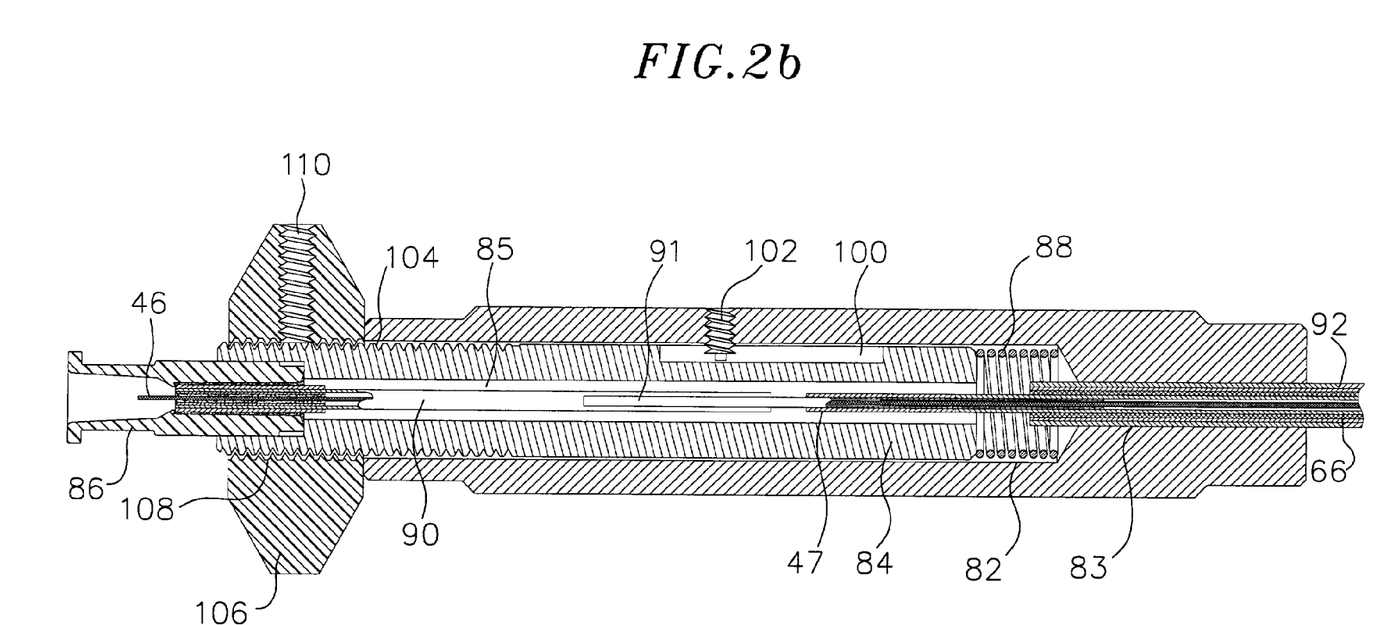
FIG. 2b is a side cross-sectional view of the needle control handle where the needle is in an extended position.

Extension and retraction of the injection needle 46 out the distal end of the tip electrode 36 is accomplished by the needle control handle 17. As illustrated in FIGS. 2a and 2b, the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the proximal end of the piston chamber to the proximal end of the outer body 80.

A piston 84, having proximal and distal ends, is slidably mounted within the piston chamber 82. A Luer connector 86 is mounted in the distal end of the outer body. The piston 84 has an axial passage 85 through which the injection needle 46 extends, as described in more detail below. A compression spring 88 is mounted within the piston chamber 82 between the distal end of the piston 84 and the outer body 80.

The proximal end of the injection needle 46 is mounted to the Luer connector 86 by means of a first rigid tube 90, preferably made of stainless steel, which has a proximal end fitted into the Luer connector. This arrangement fixedly attaches the injection needle 46 to the piston 84 so that it moves longitudinally with the piston. The first rigid tube 90 is also fixedly attached to the piston 84 and moves longitudinally with the piston. The injection needle 46 and first rigid tube 90 extend through the axial passage 85 of the piston 84. Within the axial passage 85, a second rigid tube 91, preferably made of stainless steel, has a proximal end mounted coaxially within the distal end of the first rigid tube 90. The proximal end of the second rigid tube 91 is mounted within the protective tube 47, which has its proximal end inside the axial passage 85, and the distal end of the second rigid tube is attached, directly or indirectly, to the outer body 80. The guide tube 66, through which the protective tube 47 and injection needle 46 extend, as discussed above, is fixedly attached to the outer body 80 by means of a shrink sleeve 92, as is generally known in the art.

In use, force is applied to the piston 84 to cause distal movement of the piston relative to the outer body 21, which compresses the compression spring 88. This movement causes the injection needle 46 to correspondingly move distally relative to the outer body, guide tube 66, protective tube 47 and catheter body 12, so that the distal end of the injection needle extends outside the distal end of the tip electrode 36. When the force is removed from the piston, the compression spring 88 pushes the piston 84 proximally to its original position, thus causing the distal end of the injection needle 46 to retract back into the tip electrode 36. Upon distal movement of the piston 84, the first rigid tube 91 moves distally over the second rigid tube 91 to prevent the injection needle 46 from buckling within the axial passage 85.

The piston 84 further comprises a longitudinal slot 100 extending along a portion of its outer edge. A set screw 102 extends through the outer body 80 and into the longitudinal slot 100. This design limits the distance that the piston can be slid proximally out of the piston chamber 82. When the distal end of the injection needle 46 is in the retracted position, preferably the set screw 102 is at or near the distal end of the longitudinal slot 100.

The proximal end of the piston 84 has a threaded outer surface 104. A circular thumb control 106 is mounted on the proximal end of the piston. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the injection needle 46 can be extended out the distal end of the catheter. The threaded surfaces of the thumb control 106 and piston 84 allow the thumb control to be moved closer or farther from the proximal end of the outer body 80 so that the extension distance of the injection needle can be controlled by the physician. A tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

In another preferred embodiment constructed in accordance with the present invention, two or more puller wires (not shown) are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction. Suitable deflection control handles for use with such a catheter are described in U.S. patent application Ser. Nos. 08/924,611, filed Sep. 5, 1997, entitled "Omni-Directional Steerable Catheter", 09/130,359, filed Aug. 7, 1998, entitled "Bi-Directional Control Handle for Steerable Catheter", and 09/143,426, filed Aug. 28, 1998, entitled "Bidirectional Steerable Catheter with Bidirectional Control Handle", and U.S. patent application entitled "Single Gear Drive Bidirectional Control Handle for Steerable Catheter" to Tim Bumbalough, et al., filed Apr. 10, 2000, the disclosures of which are incorporated herein by reference.

As an alternative to the above described embodiment, the puller wires (not shown) may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An injection catheter comprising:
a catheter body comprising a flexible tubing having proximal and distal ends and at least one lumen extending therethrough;
a tip section comprising a flexible tubing having proximal and distal ends, wherein the proximal end of the tip section is mounted at the distal end of the catheter body, the tip section having a first needle passage extending therethrough, wherein the first needle passage has a proximal region having a proximal diameter and a distal region having a distal diameter less than the proximal diameter;
a needle control handle at the proximal end of the catheter body;
a tip electrode mounted on the distal end of the tip section and comprising a second needle passage;
an injection needle extending through the catheter body, tip section, tip electrode and needle control handle and having a proximal end within the needle control handle and a distal end within the second needle passage in the tip electrode, wherein the injection needle is longitudinally slidable within the catheter body, tip section and tip electrode so that its distal end can extend beyond a distal end of the tip electrode; and
a needle stop mounted on a portion of the injection needle that is positioned within the proximal region of the first needle passage, the needle stop having a distal end that is sized to prevent the portion of the injection needle on which the needle stop is mounted from passing into the distal region of the first needle passage;
whereby the needle stop limits the distance that the injection needle can be extended beyond the distal end of the catheter body, and wherein the injection needle extends through a protective tube providing a fluid-tight seal surrounding the distal end of the injection needle.

2. An injection catheter according to claim 1, wherein the needle stop comprises a collar mounted in surrounding relation to the injection needle.

3. An injection catheter according to claim 2, wherein the collar has a length ranging from 0.01 inch to about 0.75 inch.

4. An injection catheter according to claim 1, wherein the needle stop comprises an elongated tube mounted in surrounding relation to the injection needle.

5. An injection catheter according to claim 4, wherein the elongated tube has a length of at least about 2 inches.

6. An injection catheter according to claim 1, where the needle stop is integral with the injection needle.

7. An injection catheter according to claim 1, where the injection needle comprises:
   a proximal tubing having proximal and distal ends and an outer diameter greater than the distal diameter of the needle passage; and
   a distal tubing having proximal and distal ends; wherein the distal end of the proximal tubing is attached to the proximal end of the distal tubing.

8. An injection catheter according to claim 1, wherein the protective tubing forms at least a portion of the needle passage.

9. An injection catheter according to claim 1, wherein a lumen extends through the needle.

10. An injection catheter according to claim 4, wherein the elongated tube is mounted around an elongated portion of the injection needle in the proximal region of the first needle passage.

11. An injection catheter according to claim 4, wherein a distal end of the elongated tube serves as the needle stop.

12. An injection catheter of claim 10, wherein the elongated tube has a diameter greater than an inner diameter of the second needle passage.

13. An injection catheter according to claim 1, wherein the injection needle is formed of a distal tubing and a proximal tubing and a distal end of the proximal tubing serves as the needle stop.

14. An injection catheter according to claim 13, wherein the proximal tubing has an outer diameter greater than an inner diameter of the distal region of the first needle passage.

15. An injection catheter according to claim 13, wherein the proximal tubing has an outer diameter greater than an outer diameter of the distal tubing.

16. An injection catheter according to claim 4, wherein the elongated tube is mounted in surrounding relation to a portion of the needle passing through the proximal region of the first needle passage, wherein a distal end of the elongated tube engages the distal region of the first needle passage to prevent the elongated tube and the portion of the injection needle on which the elongated tube is mounted from passing into the distal region of the first needle passage.

* * * * *